United States Patent [19]

Ivanov et al.

[11] 4,412,614
[45] Nov. 1, 1983

[54] THREE PANEL NEEDLED SUTURE HOLDER

[75] Inventors: Konstantin Ivanov, Edison; Jack Cascio, Bridgewater, both of N.J.

[73] Assignee: Ethicon, Inc., Somerville, N.J.

[21] Appl. No.: 349,427

[22] Filed: Feb. 16, 1982

[51] Int. Cl.³ .............................................. A61L 17/02
[52] U.S. Cl. .................................. 206/63.3; 206/388; 206/491; 229/17 R; 229/40
[58] Field of Search ...................... 206/63.3, 491, 353, 206/392, 388; 128/335.5; 242/174; 159/159; 229/17 R, 40

[56] References Cited

U.S. PATENT DOCUMENTS

| | | | |
|---|---|---|---|
| 3,857,484 | 12/1974 | Thyen | 206/63.3 |
| 3,876,068 | 4/1975 | Sonnino | 206/63.3 |
| 4,034,850 | 7/1977 | Mandel et al. | 206/63.3 |
| 4,063,638 | 12/1977 | Marwood | 206/63.3 |
| 4,069,912 | 1/1978 | Black et al. | 206/63.3 |
| 4,089,409 | 3/1978 | Cerwin | 206/63.3 |
| 4,089,410 | 5/1978 | Bolanowski et al. | 206/63.3 |
| 4,142,628 | 3/1979 | Marocco et al. | 206/63.3 |
| 4,284,194 | 8/1981 | Flatau | 206/63.3 |

Primary Examiner—Joseph Man-Fu Moy
Attorney, Agent, or Firm—Robert L. Minier

[57] ABSTRACT

A retainer for surgical sutures comprising three panels which provide for a separate needle compartment and a separate suture compartment. The panels are aligned so that once the needle has been placed in position, the winding of a suture maintains the needle in the desired position.

10 Claims, 9 Drawing Figures

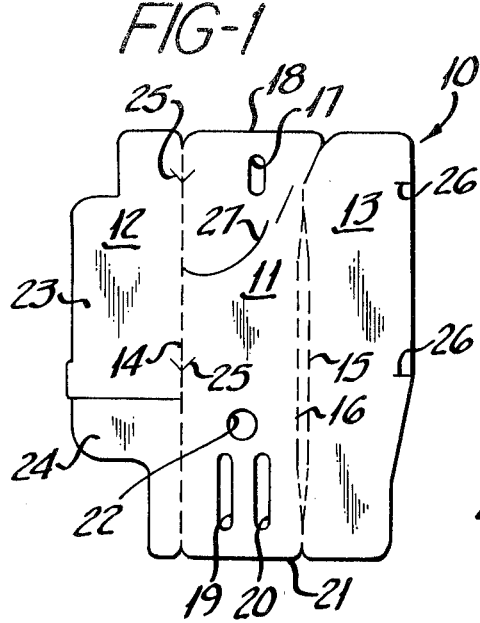
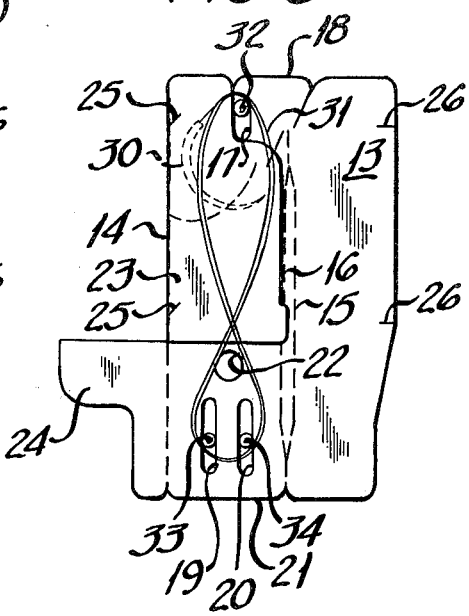
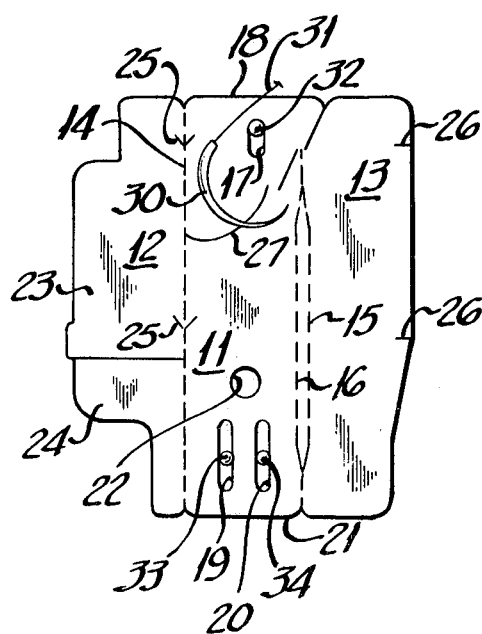
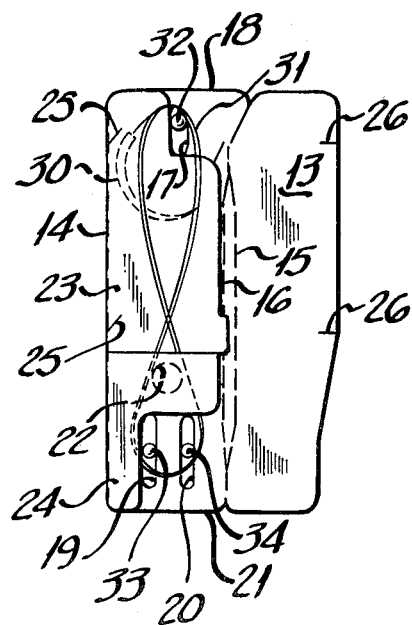

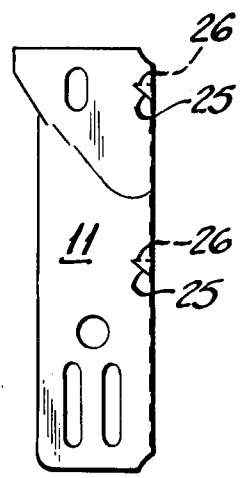
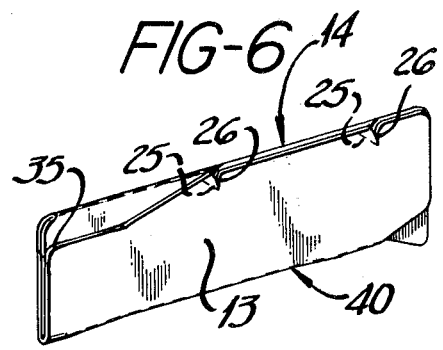
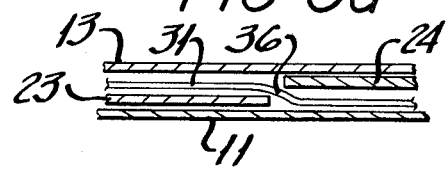
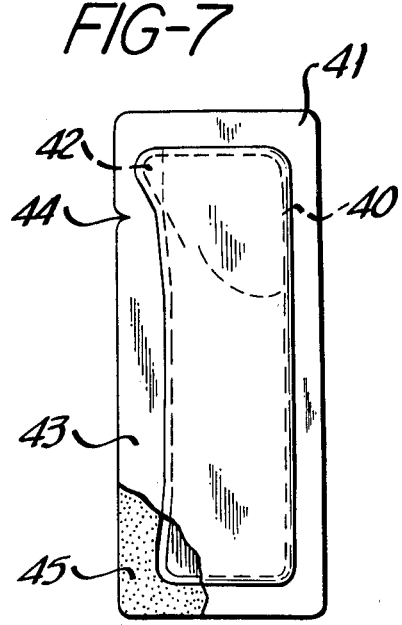
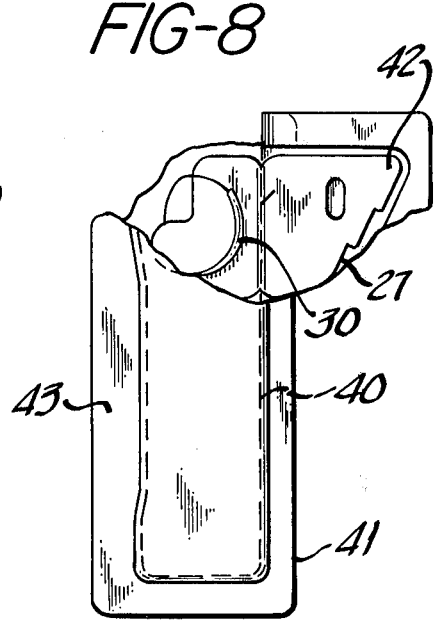

THREE PANEL NEEDLED SUTURE HOLDER

The present invention relates to holders for needled surgical sutures and, more particularly, to a multi-panel, folded retainer for a suture coil having a needle attached thereto.

Packages for surgical sutures are constructed according to the nature of the suture and its intended use. In general, the ideal package holds and protects the suture and needle during handling and storage yet allows the suture and needle to be readily removed with a minimum of handling and difficulty.

In a needled suture package it is preferred that the needle be maintained in a separate compartment to prevent the needle from cutting or damaging the suture and also prevent any dulling or damage to the sharp cutting edges of the needle. It is also preferred that the retainer for the needled suture be so constructed that when placed in a package and sterilized, and the package then presented in a sterile condition to the operating theater, it is a simple operation to open the package and present the needle to the user so it can be easily and readily gripped by a suitable instrument while all the time being maintained in a sterile condition. There are a number of suture packages which accomplish these desirable results such as those described in U.S. Pat. Nos. 3,444,944; 3,939,696; 4,014,434; 4,253,563; and 4,249,656. There are, of course, many more patents which describe various types of needled suture retainers.

In producing these suture packages, generally the retainer is placed on a plurality of pins which fit through apertures in the retainer. The retainer is slipped over the pins, the needle held in some manner and the suture wound about the pins in a FIG. 8 or like configuration. The retainer is folded in various manners to secure the needle and the wound suture within the retainer. The retainer is placed inside a foil or other package, sterilized and appropriately overwrapped to maintain sterilization.

Though many of these suture retainers have gained wide acceptance in the marketplace and in the hospital and surgical area because of the extremely efficient way they present the needled suture to the user, they apparently all suffer from some problem relating to the manufacture or the production of the wound suture in the retainer. This winding operation is usually a hand operation or, in some instances, semi-automatic and it is becoming apparent that these suture windings, because of their configuration, place undue stresses on the wrist and finger joints of the individual winding and placing the needled suture in the retainer. Apparently, in many of these retainers, pressure must be applied to the needle by one hand during the full time of winding the suture while the operator or a semi-automatic machine is winding the suture in an appropriate manner about the pins. This combination of strains being placed on both hands or wrists of the operator over extended periods of time of 6 and 7 hours a day, 5 days a week and the like, produce extreme soreness and thickness in the wrist and finger points of the operator. This strain is sufficient to either cause the operator to have to stop packaging sutures or greatly reduces operator efficiency. Also, because of the multiple folds in many of the prior art retainers and the necessity to constantly maintain the needle in position, mechanized assembly (automation) is not readily achieved.

In many of the prior art retainers, when the retainer is in its final folded configuration, it forms tubes in which the suture and needle are placed. In many instances, these tubes are open at either one or both ends. When handling such retainers to further package and process the retainer, pressure may be placed along the longitudinal edges of the retainer. When this occurs, the tubes tend to open and allow for movement of the needle and suture within the retainer and may even allow the needle and suture to fall out of the retainer. The finer and smaller the needle and suture, the greater this problem becomes. If the suture and needle fall from the retainer, the suture and needle may be rewound and all that is lost is efficiency. However, if the needle and suture merely shift in the retainer, as is usually the case, this may be unapparent to the winder and cause considerable hardship when the retainer is opened in the operating theater and an attempt made to present the needle to the surgeon. It may be that the nurse is unable to find the needle in the correct position and will have to search and grope within the retainer package for the needle and suture. This not only delays the surgical procedure but may also cause damage or blunt the sharp edges of the needle. While this may seem like a minor problem, it can become a major problem in cardiovascular or ophthalmic surgery where fine needles and sutures are most often used.

What we have discovered is an improved retainer for a needled surgical suture which has all the desirable advantages of the prior art retainers in retaining the needle and suture separate and the suture in a coiled position. Our improved retainer also allows presentation of the needled suture, when the package is opened, in a position where the needle and suture may be easily removed from the package while all the time being maintained in a sterile condition. Furthermore, our improved retainer greatly reduces the strains and stresses placed on the operator when the operator places the needled suture in the retainer and winds the suture. Our new retainer also unexpectedly is simpler in construction, easier to use and cheaper to manufacture. Because of the single construction of our new retainer and the minimum single folds required in the assembly of the retainer with the needle and suture therein, our retainer permits automation of the assembly with relatively simple mechanical motions.

Finally, our new retainer unexpectedly locks the needle and suture within their respective compartments during further processing of the retainer with the needle and suture therein. This locking occurs even when the retainer is used to hold fine needles and sutures and the locking remains when pressure is applied to the folded longitudinal edges of the retainer.

SUMMARY OF THE PRESENT INVENTION

In its broadest aspects, this invention relates to a three panel folded retainer for holding a needled surgical suture. One of the panels is sectioned to separately lock or hold the needle in place and away from the remainder of the suture and with the other section of this panel holding the suture in place without interfering with the winding of the suture. The three panels are interlockable to retain the needled suture in its desired form so that it can be handled, packaged, sterilized, transported, opened and presented for use in a sterile, easily usable form when desired.

The improved retainer for a needled surgical suture of the present invention comprises a center panel and a pair of side panels. The center panel is substantially rectangular in shape and a side panel is attached to each longitudinal edge of the center panel. The center panel has a plurality of apertures located therein. One aperture is located adjacent one of the shorter sides of the center panel and preferably a plurality of apertures is located adjacent the opposite shorter side of the center panel. These apertures are adapted to accept pins which protrude through the apertures when the retainer is placed over the pins. The suture itself is wound about these pins in the desired figure 8 or similar configuration.

One of the side panels is configured so that when it is folded on the center panel it is substantially coextensive with the center panel in the central portion of the center panel but does not cover either the single aperture or the pair of apertures located in the center panel. This side panel is sectioned transversely into two sections. This sectioning allows the needle to be placed on the center panel adjacent the single aperture and to fold the first section of the side panel onto the center panel holding the needle in place. This section of the panel is configured so as not to interfere with the winding pin. The suture is then wound from the single pin extending through the single aperture down around the double pins protruding through the double apertures. This immediately holds the sectioned side piece down on the needle and locks the needle in place so that the operator no longer is required to hold the needle. The operator now continues to wind the suture about the pins in the desired configuration. Once the suture is completely wound, the second section of this side panel is folded over holding the wound suture in place. This section of the panel is also configured so as not to interfere with the winding pins. The second side panel is substantially coextensive with the center panel and foldable about the longitudinal edge thereof. It is now a simple matter to remove the retainer from the pins and fold the second side panel on top of the first side panel to completely hold the suture and needle in place. The retainer includes means to lock the three panels together and in a preferred embodiment this locking means comprises a slit located in the unconnected longitudinal edge of the second side panel and adapted to cooperate with a complimentary locking slit disposed on the longitudinal edge connecting the center panel and the sectioned side panel to lock the needled suture in place. Because a portion of the suture is on top of the first section of the first side panel and another portion of the suture is underneath the second section of the first side panel, the junction of sections grips or hips the suture holding the suture within its compartment and, in turn, holding the needle in its compartment when the completed retainer is further processed.

BRIEF DESCRIPTION OF THE DRAWINGS

The invention will be more fully described when taken in conjunction with the accompanying drawings wherein;

FIG. 1 is a plan view of an unfolded suture retainer of the present invention;

FIG. 2 is a plan view of the unfolded suture retainer of FIG. 1 with the needle being placed on the center panel and the suture starting to be wound about the single pin;

FIG. 3 is a plan view of the suture retainer of FIG. 3 with the first section of one of the side panels folded over on the needle and with the suture being wound about the pins;

FIG. 4 is a plan view of the suture retainer of FIG. 3 with one side panel folded over the needle and the suture;

FIG. 5 is a plan view of the folded suture retainer of FIG. 4;

FIG. 6 is a perspective view of the folded suture retainer of FIG. 5 showing one means for locking the panels together;

FIG. 6a is a greatly enlarged partial cross sectional view showing a portion of the new retainer grasping and holding the suture in the retainer;

FIG. 7 is a plan view of the fully folded suture retainer of FIG. 5 contained within a sealed outer envelope; and FIG. 8 is a plan view of the suture package of FIG. 7 opened to provide access to the needled suture.

DETAILED DESCRIPTION OF THE INVENTION

FIGS. 1 through 6 illustrate the various stages in preparing a suture retainer of the present invention. FIGS. 7 and 8 show that retainer in an exemplary suture package of the present invention and its use.

In FIG. 1 there is illustrated an opened suture retainer 10 comprising a center panel 11 and a pair of side panels 12 and 13.

The center panel is generally rectangular in shape and the side panels are connected to the longitudinal edges or the longer sides of the center panel. The side panels are connected at foldable lines 14 and 15 to the longitudinal edges of the center panel. One side panel is connected at a foldable line forming a gusset 16 to provide some depth to the suture package when holding the wound suture. The center panel includes a plurality of apertures. There is one aperture 17 at the upper shorter side 18 of the center panel for accepting a pin on which a suture may be wound and there is a pair of apertures 19 and 20 adjacent the lower shorter side 21 of the center panel for accepting a pair of pins on which the suture is wound. The more centrally located aperture 22 is merely used to aid in the alignment of a plurality of the folded retainers and in identifying various suture packages.

One of the side panels 12 is separated in two sections 23 and 24 as will be explained hereinafter. The retainer also includes a plurality of complimentary slits 25 and 26 at the edges of the side panels to provide a locking means as will also hereinafter be described. The center panel includes a die cut area 27 positioned substantially diagonally across the center panel adjacent the single aperture for allowing ready exposure of the needle when it is desired that the suture be used as will be more fully described hereinafter.

In placing the needled suture in the retainer, the needle 30 is first placed as shown in FIG. 2 in the position it is desired to be in in the first package. Once the needle has been placed and the suture 31 started to be wound about the single pin 32 protruding through the single aperture, the upper section 23 of the sectioned side panel 12 is folded over on the needle as shown in FIG. 3. This sectioned area holds the needle in the desired position and removes the needle or separates the needle from the remainder of the suture so that during further processing, storage, sterilization, and transportation nothing will damage the needle or suture. The suture is then wound from the single pin over the folded section of the side panel and places pressure on section 23 to hold the needle in place. Any outside pressure being placed to hold the needle may now be removed and the suture continued to be wound. The suture is wound from the single pin down and around the double pins 33 and 34 at the lower end of the center panel. Preferably the suture is wound in a FIG. 8 configuration as shown though other winding configurations may also be used.

When the suture has been completely wound about the pins, the second section 24 of the sectioned side panel 12 is folded over the bottom portion of the sutures holding the sutures in place as is more fully shown in FIG. 4. The retainer may then be removed from the pins and the other side panel 13 is folded about the lines 15 on top of the sutures as shown in FIG. 5. This places the needle in one pocket within the three panel folder and the suture in another separated pocket of the three panel folder. Once the retainer is completely folded, it is locked as is more clearly shown in FIG. 6 by engaging the slits 26 in the unconnected longitudinal edge 35 of side panel 13 with the complimentary locking slits 25 in the folded edge 14 between the center panel 11 and the opposite side panel 12.

Though a combination of slits is shown, it is clear that other locking means may be used such as tabs at one edge which fit into slits at the opposite edge and the like.

FIG. 6a depicts the locking of the suture 31 within its compartment. A portion of the suture compartment comprises the upper surface of the first section 23 of the first side panel and the under surface of the second side 13 panel while the remainder of the compartment comprises the upper surface of the center panel 11 and the under surface of the second section 24 of the first side panel. This causes the juncture 36 where the first and second sections meet to grasp the suture and lock it within its compartment. The grasping of the suture at this juncture line coupled with the double locks as shown in FIG. 6 insure that the needle and the suture remain where placed in the retainer throughout the processing and packaging of the retainer and until the needled suture is removed from the retainer.

The suture folder of the present invention is preferably constructed of heavy weight, relatively stiff paper or paperboard such as 5 point to 12 point solid, bleached sulfate board. This paperboard is readily foldable and yet sufficiently strong and stiff to support the needled suture and provide a relatively rigid package. Similar materials, including plastics, foils, and laminates of these with each other or with paper can also be used with good results. The folder can be readily cut from such materials by a single die which also forms the desired fold lines including the necessary gusset in accordance with the present invention.

As may be seen from the prior description, once the needle is placed and the first section of the side panel folded over on the needle and the suture brought down on top of the sectioned piece to the winding pins, the operator may remove any pressure required to hold the needle in place and, hence, relieve any stress being placed on the operator's hand in holding the needle while winding the suture. The new folder works with various sized needles and once the operator has placed the needle it is a simple thing for a mechanical winder to wind the suture in a desired configuration. It is extremely difficult, if not impossible, to wind the suture first and then place the needle mechanically. This is especially true because of the large variation of needle sizes and it is difficult to mechanically retain all sizes with the same mechanism for gripping the needle. This difficulty is further compounded when winding a resilient or springy suture such as cat gut. As may be seen from the previous description, our new panel eliminates these problems in that once the operator has placed the needle and closed the sectioned panel, no matter what size the needle, a machine may then wind the suture as the needle size has no influence whatsoever on the winder. Hence, our improved folder allows for considerable automation in the packaging of sutures and greatly reduces the stresses placed on the wrist, hand, and fingers of the operator.

Referring to FIGS. 7 and 8, the fully folded retainer and needle suture 40 of FIG. 6 is subsequently sterilized and sealed within a sterile outer envelope 41 as illustrated in FIG. 7. The tab 42 projects beyond the width of the folded retainer and is secured in the seal area 43 of the envelope as illustrated. A tear notch 44 is provided in the outer edge of the envelope and located approximately opposite the lower edge of the tab of the folder to facilitate opening of the suture package by tearing the envelope. The envelope is a conventional suture package envelope formed by heat sealing the periphery of two panels of aluminum foil coated on their interior surfaces with a heat sealable polymeric composition 45 as illustrated in FIG. 7. Other means for sealing the envelope may be employed. The suture package as illustrated in FIG. 7 is sterile and hermetically sealed and may be stored for extended periods of time. When the needled suture is to be removed from the package, the outer envelope is opened by tearing the notch as illustrated in FIG. 8. Since the tab is secured in the seal line of the envelope above the notch, the die cut portion of the center panel 11 is simultaneously removed as the envelope is opened, thus presenting the needle 30. The center panel is made to tear diagonally across the width of the suture package provided by the die cut 27 and the needle thereupon exposed and readily grasped with a needle holder in order to withdraw the suture from the package as illustrated in FIG. 8.

The needled sutures packaged in the retainers of the present invention may be multifilament or monfilament sutures and the multifilament sutures may be braided, twisted, or coated.

The foregoing description has been drawn to a preferred embodiment of the present invention and many variations which nevertheless employ the essential features thereof will be apparent to those skilled in the art.

What is claimed is:

1. An improved retainer for needled surgical sutures comprising:
   (a) a center panel;
   (b) a pair of side panels;
   (c) said center panel being substantially rectangular in shape;
   (d) a side panel foldably connected to each of the longitudinal edges of the center panel;
   (e) a single aperture located adjacent one transverse edge of said center panel through which a pin may protrude on which the suture may be wound;
   (f) at least one aperture located adjacent the opposite transverse edge of said center panel through which a pin may protrude on which the suture may be wound;
   (g) one of said side panels being configured so that when it is folded upon the center panel it is substantially coextensive with the center panel in the central portion thereof but does not cover the apertures;

(h) said side panel being sectioned transversely so that the needle of the needled surgical suture may be placed on the center panel adjacent the single aperture and the first section of said side panel folded over on to the center panel to cover and enclose the needle without covering the aperture, whereby when the suture is wound about the pins protruding from the apertures the initial winding of the suture will hold the needle in place while the suture is being wound about the pins;

(i) the second section of said side panel being foldable over the center panel to contain the lower portion of the wound sutures;

(j) the second side panel being substantially coextensive with the center panel and foldable about the longitudinal edge thereof connecting said side panel to the center panel; and (k) said folder including locking means to maintain the folded panels in place and maintain the needled surgical suture in the desired configuration.

2. The retainer of claim 1 wherein there are a pair of apertures located adjacent the opposite transverse edge of the center panel through which a pair of pins may protrude.

3. The retainer of claim 1 or 2 wherein the locking means includes at least one slit located along the unconnected edge of the non-sectioned side panel which slit cooperates with a complimentary slit disposed in the longitudinal edge correcting the center panel and the sectioned side panel to lock the folded panels together.

4. The retainer of claim 3 including a gusset disposed along the longitudinal edge of the center panel connected to the non-sectioned side panel.

5. The retainer of claim 1 wherein the center panel includes a die cut extending diagonally across the width of the center panel to define a needle access section.

6. A suture package comprising in combination a folded retainer of claim 5 and a needled suture, the needle of said suture being positioned between said center panel and the first section of the sectioned side panel with a portion of the suture being coiled between the first section of the sectioned side panel and the other side panel and the remainder of the suture being coiled between the remaining section of the sectioned side panel and the center panel.

7. A suture package of claim 6 wherein the needle transverses the die cut in the center panel.

8. The suture package of claim 7 wherein the suture is coiled in a FIG. 8 configuration.

9. A suture package of claim 6 enclosed in an outer envelope sealed around the periphery thereof.

10. A suture package of claim 9 wherein a portion of the center panel at the needle access section extends beyond the folded edge of the center panel and non-sections said panel and is secured in the seal around the periphery of the outer envelope.

* * * * *